United States Patent [19]
Paltieli

[11] Patent Number: 5,647,373
[45] Date of Patent: Jul. 15, 1997

[54] ARTICULATED NEEDLE GUIDE FOR ULTRASOUND IMAGING AND METHOD OF USING SAME

[75] Inventor: Yoav Paltieli, Haifa, Israel

[73] Assignee: Ultra-Guide Ltd., Haifa, Israel

[21] Appl. No.: 333,800

[22] Filed: Nov. 3, 1994

[30] Foreign Application Priority Data

Nov. 7, 1993 [IL] Israel ........................... 107523

[51] Int. Cl.⁶ ................................ A61B 10/00
[52] U.S. Cl. ..................... 128/749; 128/662.03
[58] Field of Search ............... 128/662.03, 662.05, 128/662.06, 749–756, 20; 606/130

[56] References Cited

U.S. PATENT DOCUMENTS

| | | | |
|---|---|---|---|
| 4,407,294 | 10/1983 | Vilkomerson | 128/662.05 |
| 4,899,756 | 2/1990 | Sonek | 128/662.05 |
| 4,911,173 | 3/1990 | Terwilliger | 128/662.06 |
| 4,967,752 | 11/1990 | Blumenthal et al. | |
| 5,078,140 | 1/1992 | Kwoh | |
| 5,158,088 | 10/1992 | Nelson et al. | 128/662.05 |
| 5,170,790 | 12/1992 | Lacoste et al. | 128/662.03 |
| 5,251,127 | 10/1993 | Raab | 606/130 |
| 5,280,782 | 1/1994 | Wilk | 128/20 |
| 5,397,323 | 3/1995 | Taylor et al. | 606/130 |

FOREIGN PATENT DOCUMENTS

| | | |
|---|---|---|
| 025214 | 3/1981 | European Pat. Off. |
| 244274 | 11/1987 | European Pat. Off. |
| 276601 | 8/1988 | European Pat. Off. |
| 349686 | 1/1990 | European Pat. Off. |
| 456103 | 11/1991 | European Pat. Off. |

*Primary Examiner*—Sam Rimell
*Assistant Examiner*—Pamela L. Wingood
*Attorney, Agent, or Firm*—Frishauf, Holtz, Goodman, Langer & Chick

[57] ABSTRACT

An apparatus configured to direct a medical needle onto a target inside a living body as indicated by an ultrasound imaging device includes an ultrasound transducer and a needle guide holding the medical needle, both attached to a vertical post by movable arms, an ultrasound imaging device and a computer-controller. The arms are provided with links connected by universal joints which permit positioning by the physician of the transducer and the needle guide in any place on the body in the desired direction. The position of the components is indicated to the computer controller by sensors mounted in the joints of the arms or by wireless transmission. The transducer issues signals regarding the target point to the imaging device which transmits the information to the computer controller, the latter adjusting the angular direction of the needle trajectory onto the target. The physician places the transducer on the body in accordance with the image of the target projected on the screen of the imaging device, and places the needle point on the skin close to the target, whereupon the direction of the needle trajectory is automatically adjusted by the apparatus.

16 Claims, 6 Drawing Sheets

ARTICULATED NEEDLE GUIDE FOR ULTRASOUND IMAGING AND METHOD OF USING SAME

TECHNICAL FIELD

The present invention relates to apparatus for performing needle biopsy or aspiration by automatically controlling the movement of a medical needle as it penetrates the body guided by an ultrasound imaging device.

BACKGROUND ART

During recent years interventional ultrasound diagnosis and therapy has become widely used, and many surgical procedures have been replaced by more gentle and less time consuming needle therapy to the benefit of the patient. Inter alia, ultrasonic imaging of maternal and fetal tissues has greatly facilitated prenatal diagnosis and treatment, and ultrasound imaging devices greatly assist the physician in properly positioning a biopsy needle to perform amniocentesis, cordocentesis and trans-abdominal chorionic sampling.

There are many different biopsy techniques and needles, and the needle depends on the type of patient and the target organ. The method mostly used today is the "free hand" technique, whereby the transducer is placed at a certain distance from the entry site of the needle and the needle is manipulated with one hand. This technique requires considerable skill and frequently repeated punctures, unless the target is relatively large or located superficially. For these reasons and because manipulation of the needle as guided by an ultrasound image requires both hands of the physician, there exists the trend to design and provide automatic devices for guiding the needle as directed by the ultrasound beam.

Early developed devices include a needle attached to an ultrasound transducer housing in spaced-apart, articulated manner, thus enabling the physician to manually direct the needle onto the desired biopsy location and to insert it to the required depth. Such devices are, for instance, disclosed in U.S. Pat. No. 4,899,756 (SONEC) and U.S. Pat. No. 4,911,173 (TERWILLINGER). While all of these devices provided some movement of the needle guide and needle relative to the transducer, the physician was significantly hampered in positioning the needle prior to and during insertion, as well in positioning the transducer once the needle had been inserted into the body.

A commonly used device includes a transducer and a coaxial needle guide for manual positioning and insertion of a needle. While these devices allow rapid and convenient guided biopsy, they have several significant drawbacks: 1) the transducer must be placed directly over the lesion which requires its sterilization or its draping by sterile covering. 2) The physician is forced to hold the transducer in one hand while using the other for sterilizing and anesthetizing the biopsy site. 3) After insertion of the needle the transducer must be held by an assistant or must be removed while the needle is maneuvered. 4) Multiple passes may necessitate re-positioning of the transducer and reinsertion of the needle. 5) The existing needle guides may make it difficult to enter some superficial lesion. 6) Most slotted transducers are linear in configuration and relatively large, making some costal and subcostal approaches difficult.

A completely automatic apparatus for computer controlled stereotactic brain surgery is disclosed in U.S. Pat. No. 5,078,140 (KWOH). This apparatus is highly complicated and expensive and, for this reason, available for large institutions only. It has to be calibrated for every operation, and does not belong into the category of the present apparatus designed for multiple, daily use by any physician who need not be specially skilled in this art.

SUMMARY OF THE INVENTION

The present invention has as its main object to provide a computer-controlled needle guide enabling the physician to get to the target as close as possible.

It is another object to permit positioning of the ultrasound transducer distanced from the actual entry site thereby permitting the physician to place the needle in an optimal position.

It is still another object to direct the needle in angular alignment with the path of the ultrasound beam, so as to enable the physician to view the needle during its entire progress inside the body, in contradistinction to the existing devices and the free-hand method.

And it has a final object to permit the physician the use of both hands for insertion of the needle without the help of an assistant.

The apparatus is semi-automatic in that it requires the surgeon to place an ultrasound transducer onto the skin, into the rectum or the vagina, and the point of a medical needle onto the skin of a patient in the most suitable location as viewed on the screen of the imaging device, whereupon the angle of the needle is adjusted by computer-controlled mechanical means in a manner causing its manual or automatic insertion to hit the target.

The mechanical part of the apparatus includes a vertical cylindrical post and two articulated arms movable along and around the post. One arm includes a first horizontal link slidingly movable along and around the post by means of a sleeve at its near end and a second, allaround movable link attached to the end of the first link by a universal joint or ball-and-socket joint permitting its manual placing in any location of a patient's body.

The other arm includes a first horizontal link slidingly movable along and around the post by means of a sleeve at its near end and a second, allaround movable link attached to the end of the first link by a universal joint or ball-and-socket joint. A needle guide is attached to the end of the second link and is automatically movable in all directions and angled by servo-motors built into the different components holding the needle guide. These components include a shaft rotatably mounted in a ball-and-socket joint at the end of the second arm which also includes a servo-motor for rotating the shaft. At the end of the shaft two spaced-apart links are attached at their respective one end while their other ends are pivotally connected to two lugs on a needle guide. One of the links is rigidly attached to the shaft end and is longitudinally adjustable by a servo-motor, while the other link is pivotally attached to the shaft end, thus permitting the angular adjustment of the needle guide in one plane, while the rotary motion of the shaft serves to adjust the angle in a direction perpendicular thereto.

Insertion of the needle is either manual or, alternatively by a third servo-motor likewise controlled by computer signals.

The sleeves on the first links are provided with fixation means on the post, while all servo-motors possess magnetic brakes holding the links in their adjusted final position.

After manual setting of both arms and their links their respective angular and longitudinal motion from a zero-position is signalled to the computer by suitable sensors. The computer is preferably programmed to serve as an image processor of the ultrasound image, allowing the physician to mark the target on the computer screen. By computing the data from the position sensors and the ultrasound generating and imaging device, the computer adjusts the needle direction onto the target. The physician, while watching the process on the imaging device is able to interfere and to adjust faulty operation of the apparatus.

In a preferred embodiment of the apparatus the required trajectory of the needle onto the target may be displayed on the imaging device overlaid over the picture of the target. It is also feasable that the computer should display instructions to the physician as to the position of the needle guide and/or the transducer on the patient's body.

The position of the needle guide and the ultrasound transducer can also be determined by using wireless transmission such as radio, ultra-sound or light transmitting units, or light reflecting units, mounted on the needle guide, or on the needle itself, and on the ultrasound transducer, suitable receivers being used for transmission of the position to the computer.

A preferred method of defining the position of the ultrasound transducer while using wireless transmission includes positioning three small battery-operated infra-red ultra-sonic transponders on the ultrasound transducer in triangular alignment, each transponder having a different triggering code. A controller is provided with three spaced-apart infra-red ultra-sonic transceivers which emit coded infra-red signals to the respective transponder on the transducer and receive ultra-sonic responses from the respective transponder. The received signals are geometricaly calculated by the controller (so-called triangulation) providing the exact position of the transducer in three-dimensional space.

A similar procedure is used to direct the needle onto the target as transmitted by the ultra-sound transducer to the processing and control unit. This unit is provided with two transmitters transmitting wireless signals to two transponders mounted on the needle guide which issue signals for directing the needle in two dimensional directions, namely effecting rotational motion and angular adjustment of the needle. The transponders send their responses, thereby recording the needle position in real time.

DETAILED DESCRIPTION OF THE DRAWINGS

Figure 1:
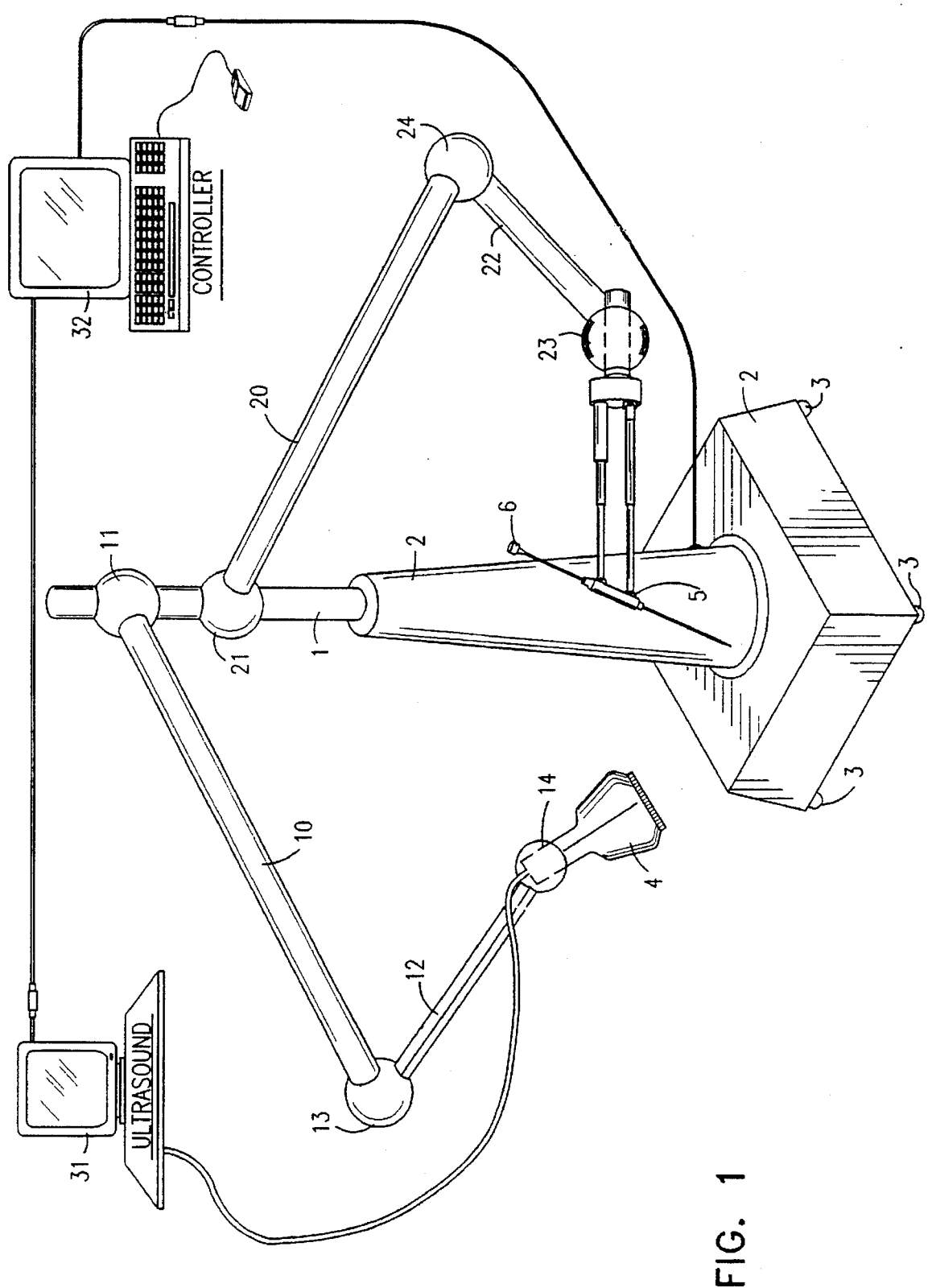
FIG. 1 illustrates the apparatus of the invention in isometric view, showing the ultrasound imaging device and a computer controller in the background.

With reference to FIG. 1 the mechanical part of the apparatus comprises a vertical, cylindrical post 1 which is firmly mounted on the floor or any other stationary support and movable thereon by means of caster wheels 3. Two arms are movable along and around the post, one arm supporting an ultrasound transducer 4 and another arm supporting a needle guide 5 and a medical needle 6. The arm supporting the transducer includes a horizontal link 10 which is movable along and around the post by means of a sleeve 11, the latter being provided with fixation means (not visible) for maintaining its exact position. A flexible link 12 is attached to the end of the horizontal link by means of a ball-and-socket joint 13 which allows the physician to place the transducer into any desired location on the patient's body, such as the skin, the rectum or the vagina. The transducer itself is attached to the end of link 12 by another ball-and-socket joint 14, permitting its angular adjustment for smooth adherence to the skin of the patient.

The transducer is electrically connected to an ultrasound generating and imaging device 31 and to a computer 32 adapted to control the motion of the needle guide.

A needle guide 5 is attached to an allaround movable link 22 of the second arm by means of a ball-and-socket joint 23 which permits the surgeon to position the needle onto a point on the skin chosen by him as the most suitable. Link 22 is attached to a horizontal link 20 by means of another ball-and-socket joint 24, while the link 20 is connected to and manually movable along and around post 1 by means of a sleeve 21, likewise provided with fixation means.

Figure 2:
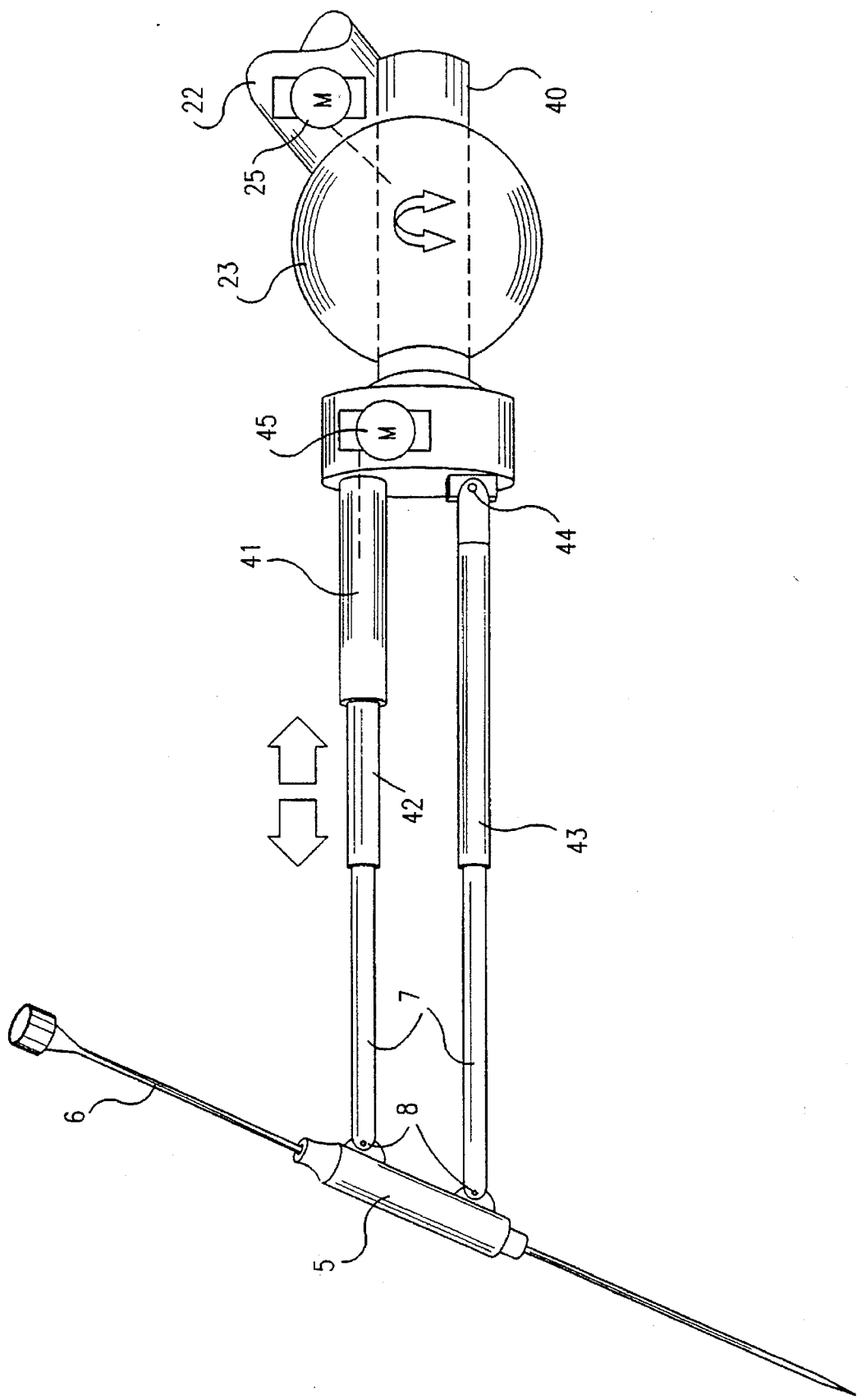
FIG. 2 illustrates a needle guide and the means for attaching it to the universal joint and for providing its angular motion.

Since it is imperative that all medical components in contact with the patient are to be completely sterile, while it is practically impossible to sterilize the entire apparatus, it becomes necessary to sterilize the needle guide while the remaining non-sterile parts of the apparatus are kept far enough from the patient's body. As shown in FIG. 2 the needle guide is provided with two long lugs 7 which are connected to the guide body by pivots 8 allowing the lugs to swing about an angle corresponding to the angle of entry into the skin.

The angular position of the needle guide 5—and the medical needle 6—is controlled by computer 32 with the aid of ultrasound device 31 by signals indicating the exact target location. The needle guide 5 is mounted in the ball-and-socket joint 23 by means of a shaft 40 which is rotatably positioned in joint 23 and adapted to be rotated by a servo-motor 25 adapted to change the angle of the needle in one sense of direction.

Angular adjustment of the needle in the second sense of direction is performed by a second, reciprocatingly acting servo-motor 45 which serves to change the length of a link 41, 42 which is firmly attached to the upper lug 7 by socket means and is at its other end rigidly connected to the end of shaft 40. The link includes a sleeve 41 which contains a bar 42 in longitudinally sliding arrangement moved in or out of the sleeve by servo-motor 45. The needle guide is additionally connected to the shaft end by a second link 43 which has its one end pivotally connected to the shaft end (44) and its other end rigidly connected to the lower lug 7 of the needle guide by socket means. By shortening or lengthening link 42 the angle of the needle axis is changed in respect of the skin surface in the plane dictated by the rotation of shaft 40, and the combined action of the two servo-motors brings the needle axis into accurate aiming position onto the target. As soon as the physician is aware of the correct position he inserts the needle into the body until the needle point is on the target as viewed on the ultrasound imaging device.

As an alternative the two lugs 7 may be rigidly attached to the needle guide and be pivotally connected to the ends of the links 42 and 43.

It is also proposed to provide an additional servo-motor which will propel the needle towards the target by a distance as controlled by the computer.

Figure 3:
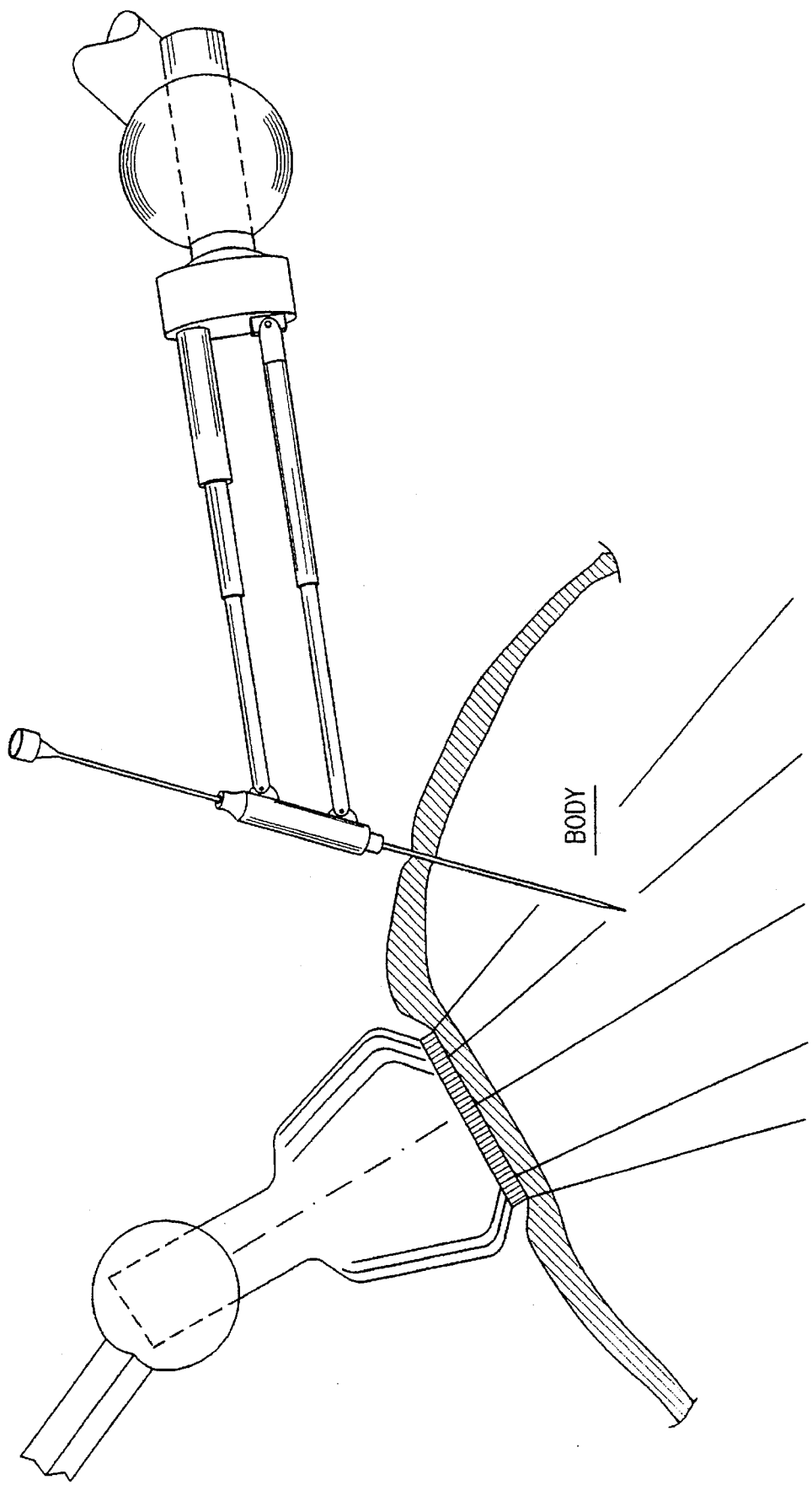
FIG. 3 illustrates a biopsy carried out with the help of the apparatus.

FIG. 3 illustrates the apparatus in action, with the needle inserted straight into the target area as indicated by the ultrasound image. The different components of the apparatus have not been numbered in this figure, since their construction has been clearly explained with reference to FIGS. 1 and 2.

Figure 4:
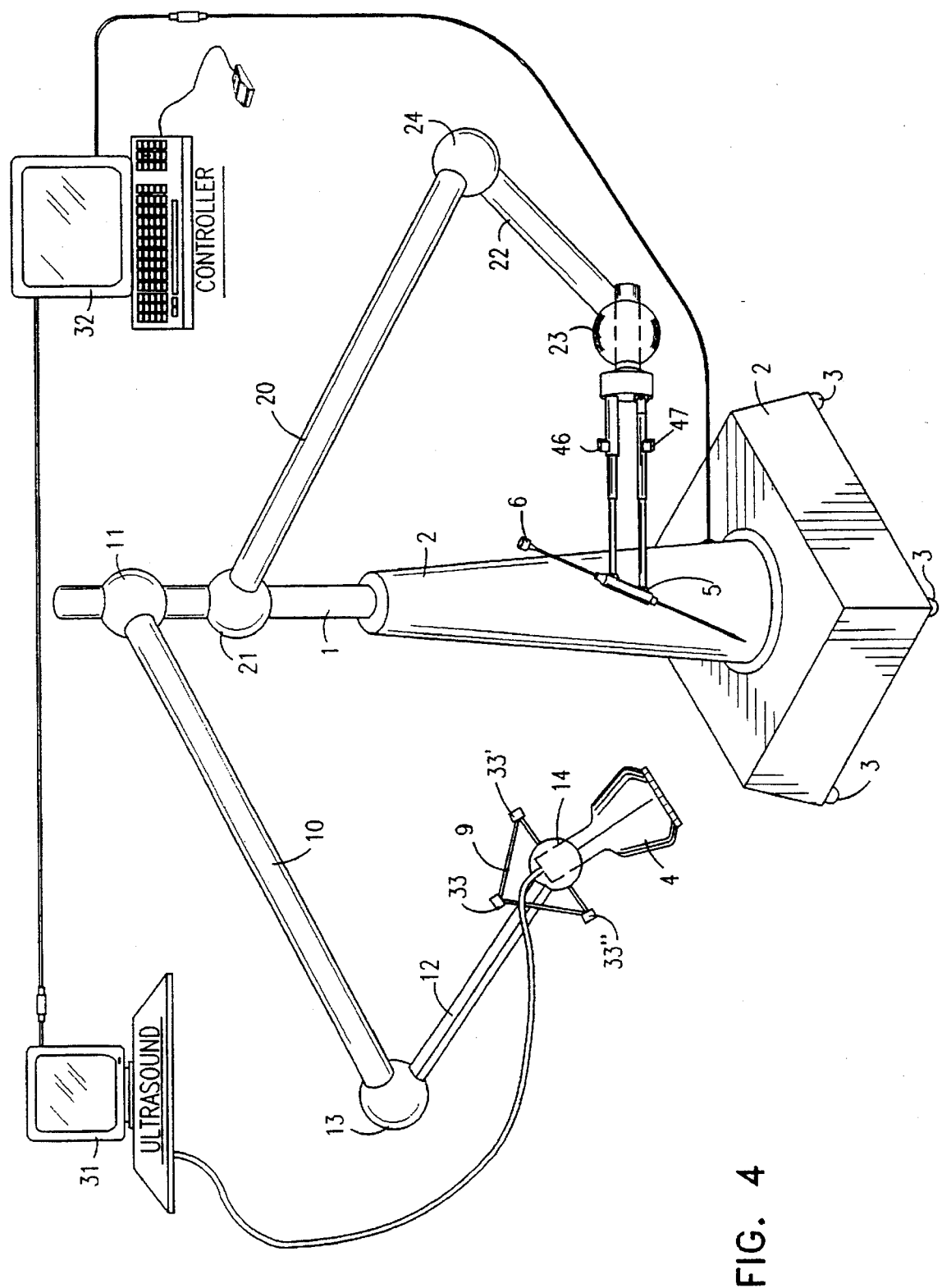
FIG. 4 is an isometric view of the apparatus illustrated in FIG. 1, provided with means for wireless transmission between transducer, controller and needle guide.
Figure 5:
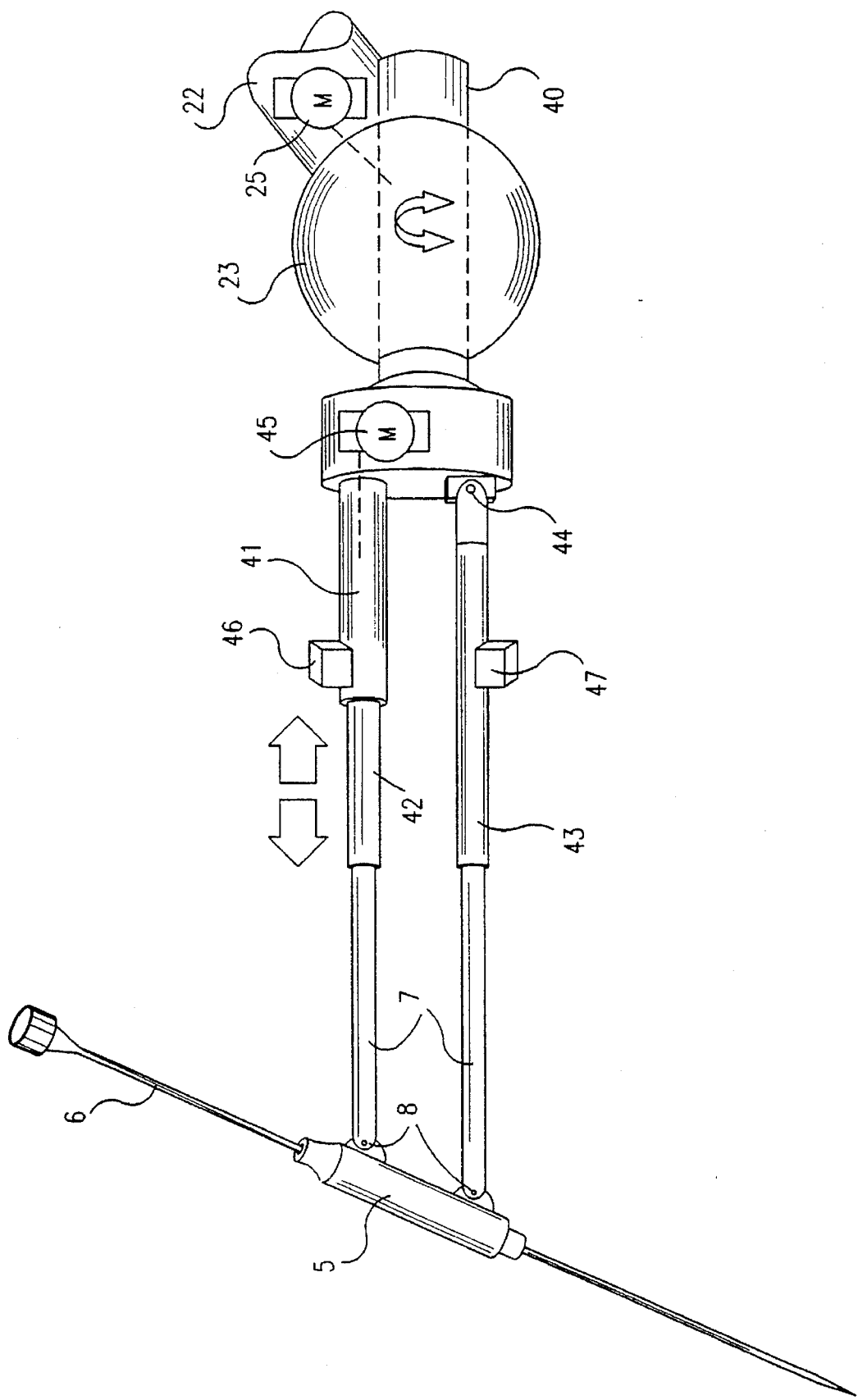
FIG. 5 illustrates the needle guide of FIG. 2, provided with means for wireless transmission.
Figure 6:
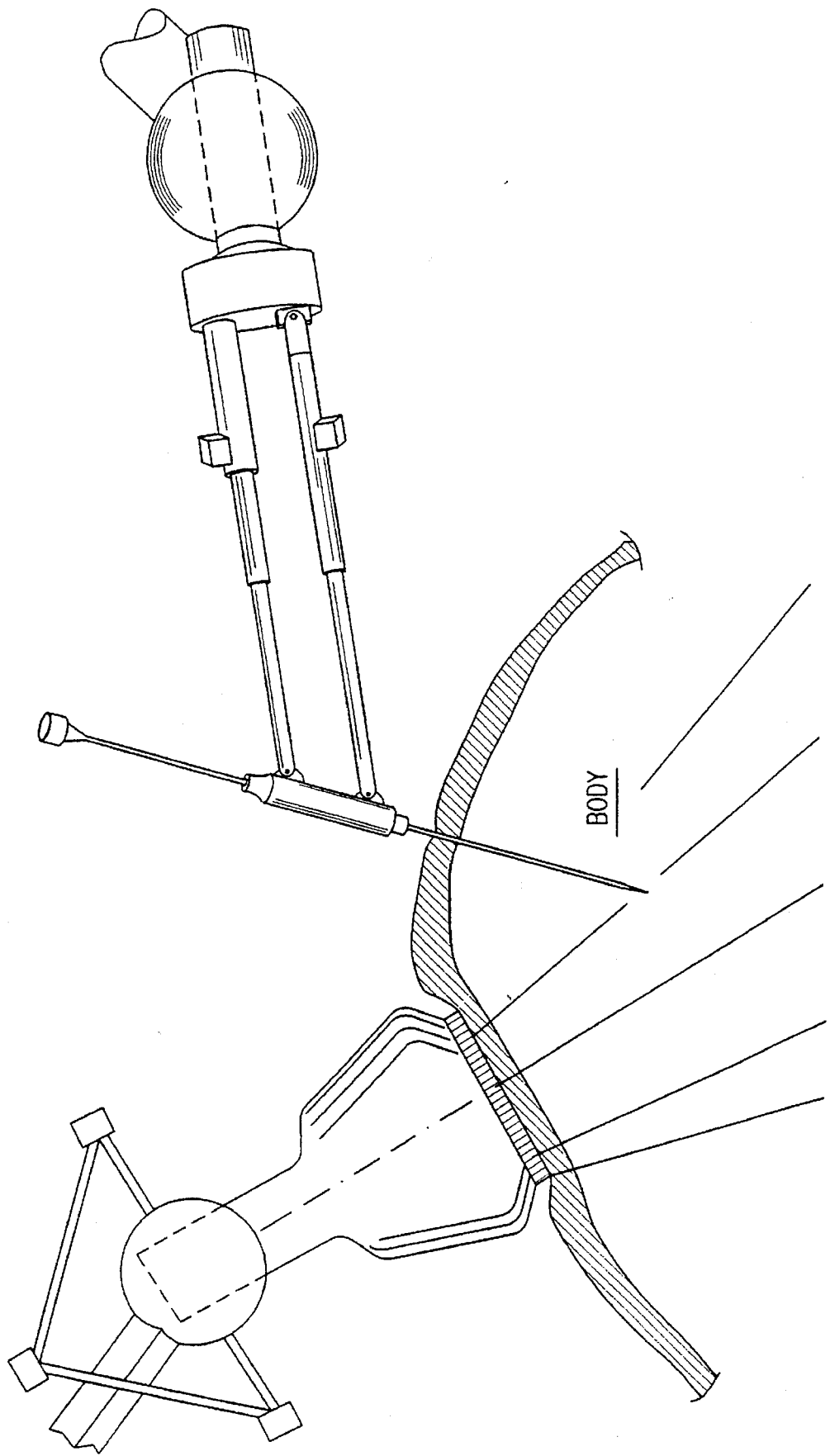
FIG. 6 illustrates a biopsy wherein both the transducer and the needle guide are provided with means for wireless transmission.

As an alternative connection between transducer 4 and the controller 32 as well as between controller and needle guide 5 is by wireless transmission. A preferred infrared-ultrasonic transmission method is indicated in respect of the apparatus illustrated in FIG. 4. Herein all components are identical with those shown in FIG. 1 with the exception that the cable between controller and needle guide has been omitted and that both the transducer and the needle guide are provided with battery-operated infrared-ultrasonic transponders. The transducer is provided with three transponders 33, 33', 33" mounted on an angular frame 9, while the needle guide is provided with two transponders 46, 47 in spaced-apart alignment. These arrangements are shown at an enlarged scale in FIGS. 5 and 6.

The controller 32 is provided with at least three spaced apart infrared-ultrasonic transceivers for communication with the transponders 33, 33' and 33", and with the needle guide. These transceivers are not shown in the drawing as known to the art. The three transponders on the transducer as well as the two transponders on the needle guide have each a different triggering code corresponding to the code emitted by the transceivers, each transceiver triggering the corresponding transponder by a coded infrared signal, whereupon the transponder emits an ultrasonic signal to the transceiver. These signals are computed so as to indicate the exact position of the transducer and of the needle guide and to energize the latter to direct the needle onto the target, the operation being identical with that described with reference to FIGS. 1 through 3.

As mentioned above the physician can see the image of the target on the ultrasound screen and, as an additional feature the required needle trajectory may also be shown on the screen, next to the image of the target.

It will be understood that the apparatus as illustrated and described herein before represent only examples of the invention, whiich may be varied and modified by a person skilled in the art, within the scope of the appended claims.

I claim:

1. Apparatus for performing needle biopsy or aspiration by automatically controlling the direction of a medical needle towards a target as indicated by an ultrasound imaging device, the apparatus comprising:

at least one post provided with means for firmly positioning the at least one post on a horizontal surface near a patient, said at least one post being provided with a vertical, cylindrical portion, a first arm for permitting manual positioning of an ultrasound transducer on any portion of a patient's body, said arm including:

a first horizontal link movable along and around said vertical portion of said at least one post, a first allaround movable link, first universal joint means for attaching one end of said first allaround movable link to said first horizontal link, an ultrasound transducer, and second universal joint means for attaching said ultrasound transducer to an opposite end of said first allaround movable link, a second arm for permitting manual positioning of a medical needle held by a needle guide on any portion of a patient's skin, said second arm including:

a second horizontal link movable along and around said vertical post portion independently of said first horizontal link, a second allaround movable link, third universal joint means for attaching one end of said second allaround movable link to said second horizontal link, a needle guide for holding said medical needle, and fourth universal joint means for attaching said needle guide to an opposite end of said second allaround movable link, a rotatable shaft for carrying said needle guide, said shaft being rotatably mounted in said fourth universal joint means, first servo motor means for rotating said shaft and said needle guide, two links connecting said needle guide to one end of said shaft and movable in a common plane defined by an angular position of said shaft, second servo motor means for changing an angle of said needle guide in said plane, an ultrasound generating and imaging apparatus connected to said ultrasound transducer, an electronic processor including computing, image processing and controlling means for computing:

a relative position of said transducer and of said needle guide, a position of the target in the patient's body from signals received from said ultrasound generating and imaging device, and a direction of said needle guide towards the target by signals issued to both of said servo motor means, and means for transmitting signals defining the position of said ultrasound transducer and of said needle guide to said electronic processor, by one of (i) a conductor and (ii) wireless means.

2. The apparatus of claim 1, wherein each of said universal joint means includes a ball-and-socket joint.

3. The apparatus of claim 1, wherein said needle guide is provided with two long, spaced apart lugs for connection to said rotatable shaft by means of said two links.

4. The apparatus of claim 3, wherein said lugs are pivotally connected to said needle guide.

5. The apparatus of claim 3, wherein said lugs are rigidly connected to said needle guide.

6. The apparatus of claim 3, wherein each of said links connecting said needle guide to said rotatable shaft includes:

a first link having one end thereof rigidly and removably attached to one lug on said needle guide and an opposite end thereof pivotally attached to said rotatable shaft, and a second link having one end thereof rigidly and removably attached to said second lug on said needle guide and an opposite end rigidly connected to said rotatable shaft, said second link having the length thereof varied by said second servo motor means, thereby changing the angular position of said needle guide and said medical needle in respect to a surface of the skin in the direction of the target.

7. The apparatus of claim 6, wherein said second link includes a sleeve and a bar slidingly movable inside said sleeve by means of said second servo motor means.

8. The apparatus of claim 1, wherein said post is mounted on a heavy base suppported by and movable on caster wheels.

9. The apparatus of claim 1,
wherein said means for transmitting signals defining the position of said ultrasound transducer and of said needle guide to said electronic processor includes:
wireless transmitting units, mounted on said needle guide and on said ultrasound transducer, and
receiving means for detecting signals issued by said wireless transmitting units, said receiving means including means for transmitting said detected signals to said processor.

10. The apparatus of claim 9, wherein said wireless transmitting units for transmitting signals defining the position of said ultrasound transducer include three spaced-apart infrared-ultrasonic transponder units, each having a different triggering code, and wherein said receiving means includes at least three spaced-apart transceivers, each configured to communicate with one of said three transponders by coded infrared signals and to compute the position of said transducer from ultrasonic responses received from said transponders.

11. The apparatus of claim 9, wherein said wireless transmitting units for transmitting signals defining the position of said needle guide include two spaced-apart infrared-ultrasonic transponders, each having a differing triggering code, and wherein said receiving means includes at least three spaced-apart transceivers, each configured to communicate with one of said two transponders by coded infrared signals and to adjust the position of said needle guide to effect a needle point thereof to be directed onto the target as indicated by said ultrasound transducer.

12. The apparatus of claim 1, further comprising:
sensor means on said first and second arms for sensing the position of each arm in relation to a predesignated zero-position and for transmitting respective signals to said electronic processor by conductor means, and
sensor means on each of said universal joint means for transmitting signals to said electronic processor by conductor means regarding the angular deviation of each said universal joint means from a predesignated zero-position.

13. The apparatus of claim 9, wherein said wireless transmitting units include one of radio transmitting units, ultrasound transmitting units, and light transmitting units.

14. Apparatus for performing needle biopsy or aspiration by automatically controlling the direction of a medical needle towards a target as indicated by an ultrasound imaging device, the apparatus comprising:
at least one post provided with means for firmly positioning the at least one post on a horizontal surface near a patient, said at least one post being provided with a vertical, cylindrical portion,
a first arm for permitting manual positioning of an ultrasound transducer on any portion of a patient's body, said arm including:
a first horizontal link movable along and around said vertical portion of said at least one post,
a first allaround movable link,
first universal joint means for attaching one end of said first allaround movable link to said first horizontal link,
an ultrasound transducer, and
second universal joint means for attaching said ultrasound transducer to an opposite end of said first allaround movable link,
a second arm for permitting manual positioning of a medical needle held by a needle guide on any portion of a patient's skin, said second arm including:
a second horizontal link movable along and around said vertical post portion,
a second allaround movable link,
third universal joint means for attaching one end of said second allaround movable link to said second horizontal link,
a needle guide for holding said medical needle, and
fourth universal joint means for attaching said needle guide to an opposite end of said second allaround movable link,
a rotatable shaft for carrying said needle guide, said shaft being rotatably mounted in said fourth universal joint means,
first servo motor means for rotating said shaft and said needle guide,
two links connecting said needle guide to one end of said shaft and movable in a common plane defined by an angular position of said shaft,
second servo motor means for changing an angle of said needle guide in said plane,
an ultrasound generating and imaging apparatus connected to said ultrasound transducer,
an electronic processor including computing, image processing and controlling means for computing:
a relative position of said transducer and of said needle guide,
a position of the target in the patient's body from signals received from said ultrasound generating and imaging device, and
a direction of said needle guide towards the target by signals issued to both of said servo motor means, and
means for transmitting signals defining the position of said ultrasound transducer and of said needle guide to said electronic processor, by one of (i) a conductor and (ii) wireless means, said means for transmitting signals defining the position of said ultrasound transducer and of said needle guide to said electronic processor includes:
wireless transmitting units, mounted on said needle guide and on said ultrasound transducer, said wireless transmitting units including one of radio transmitting units, ultrasound transmitting units, and light transmitting units, said light transmitting units including infrared transmitting units; and
receiving means for detecting signals issued by said wireless transmitting units, said receiving means including means for transmitting said detected signals to said processor.

15. The apparatus of claim 1, wherein said ultrasound generating and imaging apparatus indicates a required trajectory of said needle on a screen thereof in response to said processor.

16. The apparatus of claim 1, wherein said processor issues directions to a physician regarding interception of the target by said needle.

* * * * *